US008324448B2

(12) United States Patent
Binning et al.

(10) Patent No.: US 8,324,448 B2
(45) Date of Patent: Dec. 4, 2012

(54) LABORATORY-SELECTED COLONIES OF WESTERN CORN ROOTWORM WITH INCREASED TOLERANCE TO MAIZE CONTAINING EVENT DAS-59122-7

(75) Inventors: Rachel Binning, Clive, IA (US); Stephen Lefko, West Chester, PA (US); Timothy Nowatzki, Granger, IA (US); Stephen Thompson, Urbandale, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 124 days.

(21) Appl. No.: 12/244,845

(22) Filed: Oct. 3, 2008

(65) Prior Publication Data

US 2009/0094705 A1 Apr. 9, 2009

Related U.S. Application Data

(60) Provisional application No. 60/977,477, filed on Oct. 4, 2007, provisional application No. 61/029,958, filed on Feb. 20, 2008.

(51) Int. Cl.
*A01K 67/00* (2006.01)
*A01K 67/033* (2006.01)

(52) U.S. Cl. ............................................ 800/13; 800/8

(58) Field of Classification Search ........................ None
See application file for complete search history.

(56) References Cited

U.S. PATENT DOCUMENTS

2009/0094706 A1 * 4/2009 Binning et al. .................. 800/8

OTHER PUBLICATIONS

Storer et al., J. Econ. Entomol. 2006. 99(4): 1381-1387.*
Chege et al. Env. Entomol., 2005. 34(6): 1441-14117.*
Kim et al., Environ. Entomol. 36(3): 637-645 (2007).*
Siegfried et al., J. Econ. Entomol. 98(4): 1320-1324 (2005).*
Masson, Luke et al., "A Novel *Bacillus thuringiensis* (PS149B1) Containing a Cry34Ab1/Cry35Ab1 Binary Toxin Specific for the Western Corn Rootworm Diabrotica virgifera virgifera LeConte Forms Ion Channels in Lipid Membranes" Biochemistry 2004, 43, pp. 12349-12357.

* cited by examiner

*Primary Examiner* — Doug Schultz
(74) *Attorney, Agent, or Firm* — IPLM Group, P.A.

(57) ABSTRACT

Laboratory-selected colonies of western corn rootworm exhibiting tolerance to maize containing event DAS-59122-7 are described. Further, methods for various uses of these resistance western corn rootworm colonies are also described, including development of negative cross-resistance strategies and improved resistance management strategies.

2 Claims, 3 Drawing Sheets

LABORATORY-SELECTED COLONIES OF WESTERN CORN ROOTWORM WITH INCREASED TOLERANCE TO MAIZE CONTAINING EVENT DAS-59122-7

CROSS-REFERENCE TO RELATED APPLICATIONS

This application claims priority under 35 U.S.C. §119(e) to provisional applications Ser. No. 60/977,477 filed Oct. 4, 2007, and Ser. No. 61/029,958 filed Feb. 20, 2008, herein incorporated by reference in their entirety.

BACKGROUND OF THE INVENTION

The present invention relates to new laboratory-selected colonies of western corn rootworm (WCR, *Diabrotica virgifera virgifera*, LeConte) with increased tolerance to maize containing event DAS-59122-7, as well as methods of using such tolerant organisms and the information gathered from such organisms.

Maize (*zea mays*) is often referred to as corn in the United States. One major problem faced by growers of maize in the United States is the effects of pests, such as WCR, on the yield and standability of a particular maize crop. In an effort to combat pest infestations, various methods have been employed in order to reduce or eliminate pests in a particular plot. These efforts include rotating corn with other crops that are not a host for a particular pest, applying pesticides to the above-ground portion of the crop, applying pesticides to the soil in and around the root systems of the affected crop, and utilizing maize plants incorporating transgenic genes which cause the maize plant to produce insecticidal proteins providing protection from the target pest(s).

A recurring problem with these types of pest management strategies is the development of resistance in the pest population. If a particular pest management strategy is used for a long enough period of time, eventually pests that are resistant to the particular pesticidal strategy utilized will be selected for, and the pest population will eventually be predominantly comprised of pests with resistance to the pest management strategy. Once this occurs, the strategy or particular insecticidal tactic previously used is no longer effective, and efforts must be undertaken to determine a new method to reduce or eliminate the target pest.

Although efforts have been made to slow the development of resistance to pesticides, the evolution of resistance is generally considered inevitable when the pest management tactic applies some selective pressure. Once widespread resistance develops, the chemical (or chemical-class) that resistance has developed against is typically abandoned. The subsequent focus in the research and industrial community is to identify novel pesticides and antibiotics with different modes of action, where positive cross-resistance to previously used toxicants does not occur.

The most commonly-used strategy to manage or slow the development of resistant pests in crops is by use of a refuge. A refuge is a source for susceptible pests to survive on untreated or non-pest resistant sources. In this regard, the refuge permits susceptible pests to survive and grow to adulthood, allowing them to mate with pests exhibiting tolerance or resistance to the pest management strategy, thereby diluting the prevalence of the gene(s) conferring resistance or tolerance. Under currently-accepted guidelines, a minimum of 20% corn refuge is typically used in order that sufficient susceptible pests survive to adulthood. Of course, this method has the obvious drawback of leaving 20% of a corn crop susceptible to pest attack, thereby reducing yield substantially in those plants.

Another alternative to discarding old compounds and continually seeking new compounds is the development of negative cross-resistance strategies to control organisms containing the resistance allele. Negative cross-resistance (NCR) as a strategy for insecticide resistance management refers to a scenario where organisms tolerant to one compound are highly sensitive to another compound and vice versa. For example, if one treats an insect population with a toxin such as pesticide “A,” the number of insects carrying alleles resistant to pesticide “A” will increase in frequency. After numerous generations, insects carrying the “A” resistance allele will comprise the majority of the population. At this time a second toxin that preferentially kills those insects tolerant to the first toxin is used to treat the insect population. Use of the second toxin changes the frequency of the alleles such that the first toxin can again be used to control the insects’ population for one to several generations. By alternately deploying the two toxins, a NCR strategy can be used to maintain effective control of the pest while ‘managing’ the resistance alleles in the insect population.

In order to develop negative cross resistance strategies, however, it is necessary to be able to comparatively test susceptible and tolerant organisms to determine compounds which have a higher efficacy against resistant or tolerant organisms as compared to susceptible organisms. This problem is complicated by the manner by which resistant or tolerant pests are typically obtained, namely by direct and potentially unrealistic exposure to the toxin of interest. This type of exposure does not accurately reflect the conditions under which pests will encounter toxins in the field, however, such as in the case of toxins produced by transgenic pest resistant crops.

In addition, when resistant or tolerant organisms are available, the converse effect may be identified, namely positive cross-resistance. In this instance, organisms that are resistant or tolerant to a given toxin also show increased resistance or tolerance to another, different toxin. When this phenomenon is observed, there is a greater danger of resistance or tolerance development in the target pest, as development of resistance or tolerance to one toxin also increases resistance or tolerance to another toxin.

Resistant and tolerant organisms are also beneficial for genetic study. An understanding of the genetics that confer tolerance or resistance to a toxin can be highly beneficial in many respects, including designing new toxins or new versions of existing toxins, understanding the mechanism of resistance development, assisting in determining how resistance may be delayed from a genetic or other perspective and determining how resistance may be delayed if there are multiple and independent traits in the same target pest that confer different levels of resistance.

BRIEF SUMMARY OF THE INVENTION

Western corn rootworm colonies were selected from approximately 2,000 wild western corn rootworm insects collected from the field. The inventors believe they are the first to identify and selectively propagate colonies of western corn rootworm which are tolerant to transgenic maize event DAS-59122-7. The colonies were developed based on collections made near York, Nebr. and Rochelle, Ill. They have thus been designated the “York Selected Colony” and the “Rochelle Selected Colony,” based on the location of the original beetle collection.

This invention thus relates to western corn rootworms that exhibit increased tolerance to event DAS-59122-7. The invention further relates to beetles showing increased tolerance to event DAS-59122-7, to eggs showing increased tolerance to event DAS-59122-7, and to larvae showing increased tolerance to event DAS-59122-7. The invention further relates to the York and Rochelle Selected Colonies. This invention also relates to the descendants of all progeny resulting from mating these organisms with other colonies of western corn rootworm including derivatives of subsequent generations identifiable by their tolerance to maize containing event DAS-59122-7. This invention further relates to any use of these organisms, including the use and development of a negative cross-resistance strategy, resistance monitoring strategies, refuge deployment strategies, positive cross-resistance determinations, or determination of mechanisms of resistance, or any other use.

The invention also relates to use of such organisms in the context of a negative cross-resistance development strategy. The invention also includes use of such organisms to screen for positive cross-resistance. The invention further includes use of such organisms to determine the genetic basis for tolerance to event DAS-59122-7. The invention further relates to utilization of the organisms to develop novel resistance management strategies. The invention further relates to the use of such organisms to validate resistance management assumptions based on computer models for resistance-risk for event DAS-59122-7.

Thus, in one aspect, the invention includes a western corn rootworm in any stage that exhibits increased tolerance to event DAS-59122-7, and additionally to insects in any stage of the York Selected Colony or Rochelle Selected Colony.

In another aspect, the invention concerns mating tolerant insects, including those from either or both of the York Selected Colony or the Rochelle Selected Colony, with another colony of western corn rootworm to obtain a western corn rootworm that is tolerant to event DAS-59122-7.

In a further aspect, the invention concerns utilizing tolerant insects, including those from either or both of the York Selected Colony or Rochelle Selected Colony, to determine potential insect control strategies utilizing negative cross-resistance.

In another aspect, the invention concerns utilizing tolerant insects, including those from either or both of the York Selected Colony or Rochelle Selected Colony, to develop new resistance management strategies.

In another aspect, the invention concerns utilizing tolerant insects, including those from either or both of the York Selected Colony or Rochelle Selected Colony, to validate assumptions used in resistance risk computer simulation models.

In yet a further aspect, the invention concerns utilizing tolerant insects, including those from either or both of the York Selected Colony or Rochelle Selected Colony, to evaluate the possibility of positive cross-resistance with other existing or potential commercial corn rootworm control tactics, such as chemical insecticides or other transgenic maize events.

In other aspects, the invention concerns utilizing tolerant insects, including those from either or both of the York Selected Colony or Rochelle Selected Colony, to understand the mechanism of western corn rootworm and other *Diabrotica* spp. resistance to various insect control strategies, such as, for example, Bt toxins.

In another aspect, the invention relates to utilizing tolerant insects, including those from either or both of the York Selected Colony or Rochelle Selected Colony, as a reference to monitor populations of western corn rootworms in the field.

DETAILED DESCRIPTION

Two separate western corn rootworm colonies that exhibit tolerance to maize event DAS-59122-7 were selected via laboratory breeding process. The process by which the colonies were developed is described below.

York Selected Colony

1. The York Selected Colony was initiated by collecting approximately 6,000 western corn rootworm adults from the field near York, Nebr. in August of 2002.

2. Beetles were caged in the laboratory and approximately 30,000 eggs were collected and stored at 10° C. for 5-6 months, and then incubated at 25° C. until initial hatch was observed. Eggs were then infested onto seedling maize and reared to adults.

3. A bulk cross was made of approximately 1,000 males from York with approximately 1,000 virgin females from a non-diapausing colony of western corn rootworm. Introgressing the non-diapausing trait eliminates obligate diapause and enables more rapid cycling of rootworm population selection.

4. Eggs produced from this cross were held and allowed to hatch without undergoing a 5-6-month obligatory cold period. The result of this cross and selection for egg hatch was a half wild-type non-diapausing colony. This process initiated the York colony.

5. The York colony was first selected in May 2004 with eggs from the fifth generation after introgressing the non-diapausing trait. Approximately 12,000 Rochelle colony eggs were infested onto a seedling maize hybrid containing event DAS-59122-7 and insects were reared to adulthood. A total of 117 males and 34 females survived to adulthood during this initial generation of continuous exposure to event DAS-59122-7. This process resulted in the F1 generation of the York Selected Colony (Table 1).

6. All F1 survivors were caged together, allowed to mate, and all of their 9,707 eggs were infested back onto event DAS-59122-7 maize seedlings. Two hundred nine males and 86 females survived to adulthood during this second round of selection. This process of using DAS-59122-7 maize plants to selected for resistance in the York Selected Colony was repeated for a total of 11 generations.

On two separate instances, the number of adults recovered from selection was sufficiently low that the York Selected Colony was reared through one generation on conventional corn to provide sufficient adults and subsequent eggs to continue the selection process. This method of increasing the population size was used after the F1 and F10 selections.

Rochelle Selected Colony

1. The Rochelle colony was initiated by collecting approximately 4,000 western corn rootworm adults from a field plot of pumpkin (*Cucurbita maxima* L.) located near Rochelle, Ill. in August of 2002.

2. Beetles were caged in the laboratory and approximately 30,000 eggs were collected and stored at 10° C. for 5-6 months, and then incubated at 25° C. until initial hatch was observed. Eggs were then infested onto seedling maize and reared to adults.

3. A bulk cross was made of approximately 1,000 males from Rochelle with approximately 1,000 virgin females from a non-diapausing colony of western corn rootworm. Introgressing the non-diapausing trait eliminates obligate diapause and enables more rapid cycling of rootworm population selection.

4. Eggs produced from this cross were held and allowed to hatch without undergoing a 5-6-month obligatory cold period. The result of this cross and selection for egg hatch was a half wild-type non-diapausing colony. This process initiated the Rochelle colony.

5. The Rochelle colony was first selected in August 2004 with eggs from the sixth generation after introgressing the non-diapausing trait. Approximately 18,000 Rochelle colony eggs were infested onto a seedling maize hybrid containing event DAS-59122-7 and insects were reared to adulthood. A total of 89 males and 46 females survived to adulthood during this initial generation of continuous exposure to event DAS-59122-7. This process resulted in the F1 generation of the Rochelle Selected Colony (Table 1).

6. All F1 survivors were caged together, allowed to mate, and all of their 8,592 eggs were infested back onto event DAS-59122-7 maize seedlings. Fifty five rootworms survived to adulthood during this second round of selection. This process of using DAS-59122-7 maize plants to selected for resistance in the Rochelle colony was repeated for a total of 10 generations.

On two separate instances, the number of adults recovered from selection was sufficiently low that the Rochelle Selected Colony was reared through one generation on conventional corn to provide sufficient adults and subsequent eggs to continue the selection process. This method of increasing the population size was used after the F1 and F9 selections.

During the colony selection process, various experiments were conducted in order to ascertain the continued efficacy of DAS-59122-7 and the development of resistance or tolerance to the event. The experiments conducted are described below.

Mean survival rates were calculated from cohort-specific survival rates within a generation. Cohort survival rate was estimated by dividing the total number of recovered adults for a cohort by a weighted mean of total number of viable eggs exposed to seedlings. The mean number of viable eggs exposed for each cohort was calculated by first multiplying the number of eggs infested per container by the number of containers and by the mean hatch rate for the cohort. The number of viable eggs exposed in a generation was a weighted mean, where each cohort was weighted based on the number of containers in that cohort relative to the total number of containers for the entire generation. Mean percentage female was calculated from gender counts collected across all cohorts. For each colony and generation, adults were pooled into one cage and the number of live females was tracked weekly until the cage was terminated. Fecundity was estimated by dividing the number of total eggs per cohort by the number of live females. This estimate was standardized across colonies and generations using female and egg values from the week beginning two weeks after the maximum number of live females was recorded. Most often the same cohort of eggs used to estimate fecundity was used to estimate fertility. Otherwise, fertility was calculated from the nearest cohort in time. Fertility estimates resulted from an average within the weekly cohort.

Table 1 reports generational estimates for Rochelle-S and York-S, whereas unselected colony traits were reported as across-generation means. Life history trait information was collected from all selected colony cohorts across the lifespan of adults, whereas large insect numbers in unselected colonies limited data collection to one cohort. This difference in the way adult life history trait information was collected prevented statistical analyses. Table 1 identifies gross differences in measured traits among colonies and can be used to improve biological or genetic parameter estimates used in computer models simulating the rootworm and DAS-59122-7 system.

TABLE 1

| | Rochelle-S | | | | | York-S | | | | |
|---|---|---|---|---|---|---|---|---|---|---|
| Generation Evaluated[1] | Eggs exposed | Mean Survival Rate[2] | Percentage Female[3] | Fecundity[4] | Fertility[5] | Eggs exposed | Mean Survival Rate[2] | Percentage Female[3] | Fecundity[4] | Fertility[5] |
| F1 | 8,592 | 1.3 | 34.1 | 16.8 | 40.3 | 9,707 | 0.4 | 31.4 | 11.6 | 18.0 |
| F2 | 47,000 | 2.5 | — | — | — | 48,500 | 8.5 | 30.7 | 18.9 | 39.0 |
| F3 | 61,255 | 7.4 | 48.2 | 5.1 | 45.3 | 39,863 | 2.9 | 34.6 | 17.8 | 39.0 |
| F4 | 40,110 | 6.4 | 43.9 | 9.6 | 43.0 | 13,100 | 1.6 | 23.9 | 26.0 | 38.6 |
| F5 | 60,000 | 15.9 | 35.5 | 10.0 | 44.0 | 41,493 | 8.9 | 36.3 | 12.6 | 42.3 |
| F6 | 77,000 | 12.7 | 36.4 | 10.3 | 41.6 | 53,800 | 15.4 | 28.4 | 10.3 | 51.0 |
| F7 | 82,000 | 12.3 | 29.7 | 7.4 | 34.0 | 79,100 | 7.0 | 27.4 | 12.7 | 47.0 |
| F8 | 94,000 | 16.7 | 37.8 | 12.5 | 54.0 | 79,000 | 11.6 | 31.7 | 6.6 | 31.0 |
| F9 | 91,000 | 19.7 | — | — | — | 94,000 | 23.4 | 31.6 | 9.7 | 43.0 |
| F10 | 84,000 | 13.7 | — | — | — | 91,000 | 17.9 | — | — | — |
| F11 | — | — | — | — | — | 84,000 | 15.6 | — | — | — |
| Across Generation Mean (SD) | | 10.8 (6.17) | 38.0 (6.23) | 10.2 (3.73) | 43.2 (6.02) | | 10.3 (7.28) | 30.7 (3.74) | 14.0 (5.91) | 38.8 (9.6) |

TABLE 1-continued

|  | Rochelle-US | | | | York-US | | | |
|---|---|---|---|---|---|---|---|---|
|  | Mean Survival Rate[2] | Percentage Female[3] | Fecundity[4] | Fertility[5] | Mean Survival Rate[2] | Percentage Female[3] | Fecundity[4] | Fertility[5] |
| Across Generation Mean (SD) | 76.2 (29.34) | 53.0 (4.40) | 18.6 (9.32) | 34.5 (7.59) | 82.7 (45.88) | 49.6 (7.08) | 25.6 (6.68) | 40.1 (11.16) |

[1]Life history trait measures were collected from the progeny surviving F rounds of selection; for example, F1 measures were collected from rootworm surviving the first round of selection.
[2]Survival rate estimates reported as the percentage of viable eggs producing adults using continuous exposure to either DAS-59122-7 (selected) or isoline (un-selected).
[3]Number of females are reported as a percentage of the total number of adults.
[4]Fecundity estimates are reported as the mean number of eggs/female/day.
[5]Fertility estimates reported as percentage of eggs hatching in a subsample greater than 100 eggs.

A sublethal seedling assay (SSA) was used to characterize larval population development for Rochelle-US, Rochelle-S, York-US and York-S colonies using isoline (susceptible) and DAS-59122-7 maize. The SSA uses rate of larval population development while feeding on maize roots as a measure of rootworm susceptibility to different types of maize. The SSA provides ecologically relevant larval exposure to facilitate sensitive measures of change in larval population susceptibility.

Samples of eggs from each generation of each colony were evaluated on both DAS-59122-7 and isoline using the SSA. Three experimental units (containers) of the SSA were made for each colony by maize-type evaluation. The assay duration was 17 days, after which larvae were extracted into alcohol using a Berlese funnel. Extracted larvae were distributed across the bottom of a flat pan marked with a grid pattern. A sub-sample of larvae were collected from each experimental unit by randomly sampling squares for all larvae within a square until 25 or 30 total larvae were collected. Each colony was evaluated on DAS-59122-7 and isoline seedlings at the same time using the same rearing and environmental conditions. However, different WCR developmental rates on DAS-59122-7 and isoline maize led to running the SSA for different colonies on different dates.

Tables 2 and 3 report the colony and generational assays using the SSA technique. Table 2 shows the mean percentage of larvae in each instar for Rochelle-US and Rochelle-S 17 days after egg hatch on DAS-59122-7 maize in the sublethal seedling assay test system, and Table 3 shows the mean percentage of larvae in each instar for York-US and York-S 17 days after egg hatch on DAS-59122-7 maize in the sublethal seedling assay test system. Only the F1 and F2 generations of York-S were not evaluated on isoline and are not part of York-S across generation means reported in Table 3.

TABLE 2

| Generation evaluated | Mean percentage of larvae in each instar[1] | | | | | | Quantile correlation | | P value (H0: $\rho \geq$ |
|---|---|---|---|---|---|---|---|---|---|
|  | Rochelle-US | | | Rochelle-S | | | | | |
|  | 1st | 2nd | 3rd | 1st | 2nd | 3rd | $\rho 0^2$ | (Upper 95% CL)[3] | $\rho 0)^4$ |
| F0 | 9.0 | 64.0 | 27.0 | — | — | — | — | — | — |
| F1 | 6.7 | 76.0 | 17.3 | 5.3 | 46.7 | 48.0 | 0.78 | 0.64 (0.73) | 0.002 |
| F2 | 6.7 | 76.0 | 17.3 | 0.0 | 57.3 | 42.7 | 0.78 | 0.55 (0.65) | <0.001 |
| F3 | 10.7 | 77.3 | 12.0 | 4.0 | 64.0 | 32.0 | 0.71 | 0.62 (0.71) | 0.057 |
| F4 | 32.0 | 62.7 | 5.3 | 12.0 | 61.3 | 26.7 | 0.81 | 0.65 (0.73) | <0.001 |
| F5 | 5.6 | 75.6 | 18.9 | 0.0 | 22.2 | 77.8 | 0.58 | 0.42 (0.54) | 0.014 |
| F6 | 13.3 | 76.0 | 10.7 | 0.0 | 37.3 | 62.7 | 0.74 | 0.52 (0.63) | <0.001 |
| F7 | 12.0 | 76.0 | 12.0 | 1.3 | 54.7 | 44.0 | 0.68 | 0.53 (0.63) | 0.007 |
| F8 | 1.3 | 76.0 | 22.7 | 0.0 | 25.3 | 74.7 | 0.88 | 0.34 (0.48) | <0.001 |
| F9 | 17.3 | 73.3 | 9.3 | 1.1 | 48.9 | 50.0 | 0.73 | 0.54 (0.65) | <0.001 |
| F10 | 7.9 | 89.9 | 2.2 | 0.0 | 61.1 | 38.9 | 0.57 | 0.30 (0.44) | <0.001 |
| Across generation mean (SD) | 11.1 (8.13) | 74.8 (7.12) | 14.1 (7.39) | 2.4 (3.87) | 47.9 (15.03) | 49.8 (17.08) |  |  |  |

[1]Besides F7 un-selected using 50 larvae, all other larval percentage estimates are based on a sub-sample of 75 or 90 larvae.
[2]$\rho 0$ = The largest correlation value used in the Q-Q analysis that results in no difference (P > 0.05) among within-generation un-selected experimental units.
[3]Correlation, and upper 95% confidence limit, between un-selected and selected instar quantiles for each generation.
[4]The quantile analysis tested whether the correlation between un-selected and selected strains was equal to or greater than the corresponding $\rho 0$.

TABLE 3

| Generation Evaluated | Mean percentage of larvae in each instar[1] | | | | | | Quantile correlation | | P value (H0: $\rho \geq$ |
|---|---|---|---|---|---|---|---|---|---|
|  | York-US | | | York-S | | | | | |
|  | 1st | 2nd | 3rd | 1st | 2nd | 3rd | $\rho 0^2$ | (Upper 95% CL)[3] | $\rho 0)^4$ |
| F0 | 6.0 | 61.0 | 33.0 | — | — | — | — | — | — |
| F1 | 6.7 | 82.7 | 10.7 | 1.3 | 70.7 | 28.0 | 0.79 | 0.56 (0.66) | <0.001 |

TABLE 3-continued

| Generation Evaluated | York-US 1st | 2nd | 3rd | York-S 1st | 2nd | 3rd | $\rho 0^2$ | Quantile correlation (Upper 95% CL)[3] | P value (H0: $\rho \geq \rho 0$)[4] |
|---|---|---|---|---|---|---|---|---|---|
| F2 | 6.7 | 82.7 | 10.7 | 1.3 | 68.0 | 30.7 | 0.79 | 0.53 (0.64) | <0.001 |
| F3 | 1.3 | 56.0 | 42.7 | 0.0 | 14.7 | 85.3 | 0.79 | 0.39 (0.52) | <0.001 |
| F4 | — | — | — | — | — | — | — | — | — |
| F5 | 8.0 | 81.3 | 10.7 | 1.3 | 64.0 | 34.7 | 0.84 | 0.51 (0.62) | <0.001 |
| F6 | 6.7 | 74.4 | 18.9 | 0.0 | 40.0 | 60.0 | 0.56 | 0.47 (0.59) | <0.001 |
| F7 | 12.0 | 81.3 | 6.7 | 0.0 | 38.7 | 61.3 | 0.60 | 0.33 (0.47) | <0.001 |
| F8 | 4.0 | 85.3 | 10.7 | 0.0 | 42.7 | 57.3 | 0.74 | 0.36 (0.50) | <0.001 |
| F9 | — | — | — | — | — | — | — | — | — |
| F10 | 10.7 | 81.3 | 8.0 | 0.0 | 26.7 | 73.3 | 0.65 | 0.51 (0.62) | 0.019 |
| F11 | 8.9 | 87.8 | 3.3 | 0 | 5.1 | 48.9 | 0.70 | 0.35 (0.48) | <0.001 |
| Across generation mean (SD) | 7.1 (3.09) | 77.4 (10.58) | 15.5 (12.61) | 0.4 (0.65) | 41.2 (23.28) | 53.3 (19.57) | | | |

[1] 75 or 90 larvae were used to describe the age structure of the un-selected or selected strains for each generation.
[2] $\rho 0$ = The largest correlation value used in the Q-Q analysis that results in no difference (P > 0.05) among within-generation un-selected experimental units.
[3] Correlation, and upper 95% confidence limit, between un-selected and selected instar quantiles for each generation.
[4] The quantile analysis tested whether the correlation between un-selected and selected strains was equal to or greater than the corresponding $\rho 0$.

A total of 6 greenhouse efficacy experiments were conducted periodically across generations to determine if selection changed the injury potential of Rochelle-S and York-S on DAS-59122-7 roots. The injury potential of Rochelle-S was evaluated after the F1, F2, F5, and F10 generations of selection. The injury potential of York-S was evaluated after the F1, F2, F6, and F11 generations of selection. Two unique test systems were utilized across experiments: a seedling root trainer bioassay and a large pot bioassay. Root trainers were used to characterize the injury potential of Rochelle-S F1 and F2 generations.

The experimental unit was a single rootworm-infested maize plant. The experimental design consisted of 4 treatments arranged in a randomized complete block design with 4 replications. The experiment was repeated on 6 consecutive dates each initiated at 7-d intervals. On each date, kernels of both hybrids were planted individually in 3.8×5×20 cm cells of Rootrainers (Hummert International, Earth City, Mo.) containing a soil-less potting mix formulated for greenhouse use. At growth stage V2, a herbicide leaf-painting technique was performed on each DAS-59122-7 seedling to verify presence of the herbicide selectable marker linked with DAS-59122-7. Plants with symptoms of herbicide injury (not containing DAS-59122-7) were removed from the experiment. Thirteen days after planting, each seedling was infested with 100 eggs of the appropriate insect colony pre-incubated to hatch within 7 days of infestation. Eggs were infested to each trainer cell using a variable rate pipette calibrated to deliver the desired quantity of eggs suspended in a 0.08% agar solution. Nineteen days after infestation, plants were extracted from the trainers and the root systems visually scored for injury using the 0-3 node-injury scale (Oleson et al. 2005).

The large pot test system was used in the remaining 5 greenhouse efficacy experiments. The experimental unit was a single rootworm-infested maize plant growing in a 7.5 L pot. The experimental design for each pot experiment consisted of 4 treatments arranged in a randomized complete block design with 5 replications. Treatments included in each pot experiment are shown in Tables 5 and 6. Each pot experiment was initiated by planting kernels of each hybrid into flats filled with a soil-less potting mixture. Ten days after planting, the DAS-59122-7 seedlings were leaf painted to verify presence of the selectable marker and plants showing symptoms of herbicide injury were discarded. Seedlings were then removed from the flats and individually transplanted into 7.5 L pots 12-13 d after planting. Infestation dates and the number of eggs infested per seedling are shown in Tables 5 and 6. Egg viability for all experiments was determined using the hatch test method described previously. Infested plants were maintained in the greenhouse with regular watering until first beetle emergence was detected in the pots. The root systems were then extracted from the pots, washed with pressurized water, and the amount of root injury scored using the 0-3 node-injury scale (Oleson et al. 2005). Tables 5 and 6 report the dates roots were evaluated for each pot experiment.

A non-parametric quantile-quantile (Q-Q) analysis was used to contrast rates of larval population development (Nowatzki et al. submitted, Johnson and Wichern 2002). The Q-Q analysis uses pair-wise comparisons of the quantiles of unselected and selected strains of WCR by colony. In this analysis, the 1st through 100th quantile values (0.01, 0.02 . . . 0.99, 1.00) were calculated for each data set. If un-selected and selected colonies are similar in their susceptibility to DAS-59122-7, then the quantiles of the unselected colony should be highly correlated with the quantiles of the corresponding selected colony. For each population and generation tested, an appropriate $\rho 0$ value was determined using three replicate data sets from the unselected colony developing on DAS-59122-7. Quantiles were calculated for each replicate and an iterative process was used to identify the largest $\rho 0$ value that resulted in no significant difference (P>0.05) among the three experimental units. This iterative method of estimating an appropriate $\rho 0$ from un-selected WCR on DAS-59122-7 incorporates test system variation and decreases the Type I error rate. For each generation, the null hypothesis was that the true correlation between unselected and selected larval samples for either colony is greater than or equal to $\rho 0$.

Change in realized heritability ($h^2$), or the proportion of total phenotypic variation attributable to additive genetic variation, was estimated from change in the distribution of instars between unselected and selected colonies over generations for both Rochelle and York using the method described by Tabashnik (1992). The distribution of instars for each colony at each generation was estimated using a lognormal distribution. The $\log_e$ of the median instar and its associated standard deviation were estimated from lognormal distribution fits using the lognormal option of the Empirical CDF routine in Minitab® Release 14.12.0 (Minitab Inc, 2004). Realized heritability ($h^2$) was estimated by comparing the selected colony (-S) to the susceptible colony (-US) for each location. The susceptible colonies (-US) served as a reference that was subjected to all of the environmental and handling selection pressures as the selected (-S) colonies. Heritability was calculated for each generation and location as $h^2=R/(iS)$ where R was calculated as $R=(\log_e(\text{median-S})-\log_e(\text{median-US}))/n$, "i" was the selection intensity which was assumed to be 1 since all instars were present in each sample, and S was the average standard deviation associated with the instar distributions that was estimated as $1/(0.5*(\text{slope-US}+\text{slope-S}))$ that gives the total phenotypic variation of the instars. The results were then tabled and plotted over generations by colony.

Node-injury scores from each greenhouse efficacy experiment were analyzed using the general linear model procedure in SAS (SAS 2006) to test for differences in injury potential between treatments. Within each efficacy experiment, treatment means were compared with a t-test (P=0.05) on the differences of least squares means (PDIFF) in SAS. The percentage consistency (percentage of roots with node-injury scores of 0.00-0.25, 0.26-0.50, 0.51-0.99, 1.00-1.99, and 2.00-3.00) within treatments was also calculated. Additionally, mean node-injury scores adjusted for the number of viable eggs infested (node-injury score per 100 viable eggs infested) were also calculated to allow for a relative comparison of injury potential of the selected colonies across generations of selection.

Results from selected colony experiments were used to test whether or not founding Rochelle and York populations may have contained putative resistance. For the purpose of this assessment, putative or major resistance is assumed to be conferred by a rare, single, and recessive allele (r); three possible genotypes may occur at the locus, namely, SS, rS and rr. Only homozygous resistant individuals are assumed to be able to develop and survive on DAS-59122-7. In this study, the effective size of the founder populations was assumed to be sufficiently large to include the r allele. The hypothesis, that r was present in the founding populations, was tested by simulating changes in the frequency of r alleles using hypothesis-specific parameters and the standard genetic model following Fisher's Fundamental Theorem of Natural Selection (Fisher 1930). Li (1967) provided a mathematical formula for iterative use in describing changes in genotypic frequency with selection:

$$\Delta q = \frac{pq(q(Wrr - WrS) + p(WrS - WSS))}{(p^2 WSS + 2pq WrS + q^2 Wrr)}$$

where p is the r allele frequency, q is the S allele frequency and Wrr, WrS and WSS are the fitness parameters of rr, rS and SS genotypes, respectively. Li's equation was used iteratively $(q(t+1)=q(t)+\Delta q)$ to calculate allele frequencies over t generations (York: t=11, Rochele t=10). Mean population fitness (WM) was estimated for each generation using the standard equation of Hartl and Clark (1989):

$$W_M = p^2 Wrr + 2pq WrS + q^2 WSS$$

Simulated mean population fitness was contrasted to observed mean population fitness. Observed mean population fitness on DAS-59122-7 was the selected colony survival rate adjusted up assuming the survival rates of the unselected colony on isoline maize was mean population fitness equal to 1.0. Normal test system survival rate was estimated from across generation means of the Rochelle-US and York-US populations (Table 1). Contrasts between observed and simulated mean population fitness across generations of selection were made using a Chi-Square test, where the variance term used in the denominator was the sum of standard deviations for observed survival rates.

Figure 2:
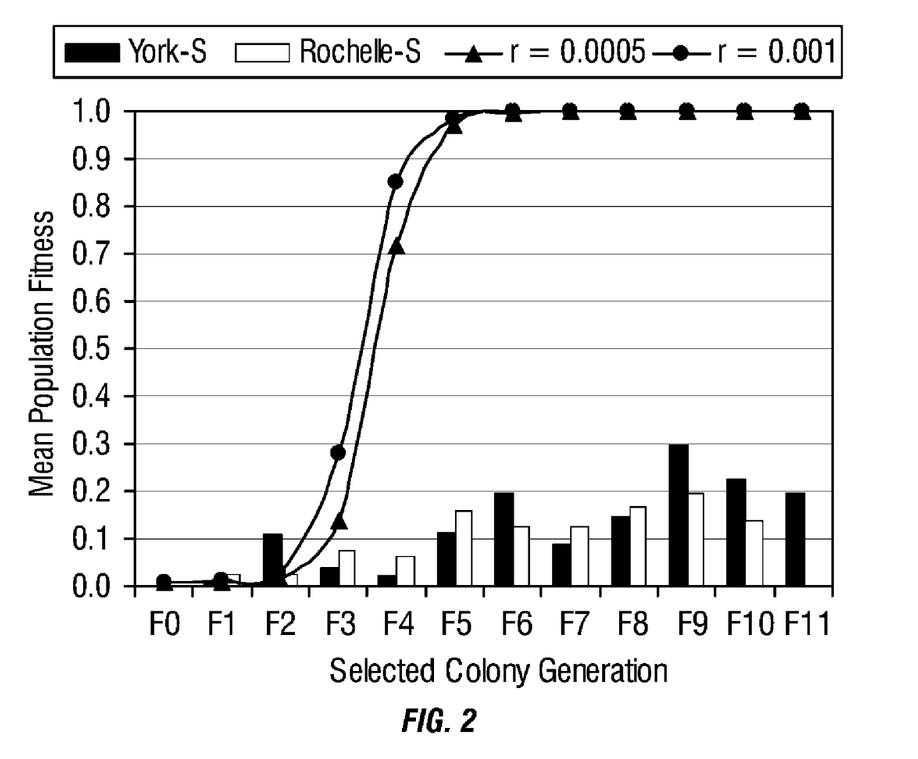
FIG. 2 compares observed (columns) mean population fitness of Rochelle-S and York-S colonies across generations of selection with DAS-59122-7 plotted with expected mean population fitness (lines) of the same colonies assuming they contained alleles for a putative major resistance gene.

The fitness of these genotypes on DAS-59122-7 was calculated assuming that 1 in 150 plants in the selection scheme was an off-type or did not contain DAS-59122-7. Therefore, the fitness values (W) of SS and rS genotypes are the weighted average of 1/150 fitness on unprotected plants and 149/150 DAS-59122-7 plants. The mortality rate of a susceptible population of WCR using realistic exposure scenarios was estimated at 99.75%, or W=0.0025 (Storer et al. 2006). Adjusted for (1/150) off-type seeds, this value increases to 0.0092. Fitness of the rS genotype (also dominance (h) of the r allele) was assumed to be 0.08; adjusted for (1/150) off-type seeds this value increases to 0.0862. Assumed fitness of the rr genotype was 1.0. These results are illustrated in FIG. 2.

Table 4 describes the normal developmental rate of all colonies on isoline maize; after 17 days there was less than 1% of larvae still in the first instar, 4.9 to 18.2% in the second instar and 81.6 to 95.1% in the third instar. Rochelle-US and Rochelle-S colonies developed at similar rates on isoline, and York-US and York-S colonies developed at similar rates on isoline. One trend was an increased and less variable rate of larval development for both York colonies compared to both Rochelle colonies.

TABLE 4

| Colony | Across generation mean (SD) percentage of larvae in each instar | | |
|---|---|---|---|
| | $1^{st}$ | $2^{nd}$ | $3^{rd}$ |
| Rochelle-US | 0.6 (2.01) | 13.2 (21.63) | 86.2 (23.57) |
| Rochelle-S | 0.1 (0.42) | 18.2 (16.97) | 81.6 (17.17) |
| York-US | 0.0 (0.00) | 4.9 (4.19) | 95.1 (4.16) |
| York-S | 0.0 (0.00) | 7.2 (5.26) | 92.8 (5.26) |

In Rochelle-US, there was no visible generational trend for change in the rate larval development as a potential result of inbreeding depression or genetic drift that may have resulted from bottlenecking this colony each generation. Rochelle-S on DAS-59122-7 produced more larvae in later instars compared to the corresponding Rochelle-US colony on DAS-59122-7 in every generation except F3 (P=0.57) (Table 2). This change in the rate of larval development is indicative of selecting for increased WCR tolerance to DAS-59122-7. Tolerance in Rochelle-S was apparent after the first round of selection (F1). After 17 days, the percentage of first and second instars in Rochelle-US was 76.0 and 17.3% compared to 46.7 and 48.0% in Rochelle-S. After F1, tolerance in Rochelle-S to DAS-59122-7 appeared variable around an intermediate level (Table 2). A high level or complete Rochelle-S resistance to DAS-59122-7 might have resulted in SSA results similar to Rochelle-US or Rochelle-S colony development on isoline (Table 4). Instead, Rochelle-S resulted in an across-generation average of 49.8% of larvae in the third instar when exposed to DAS-59122-7 instead of the 86.2 or 81.6% measured when Rochelle-US and Rochelle-S were exposed to isoline maize, respectively (Table 2). After F1, there was no consistent trend for increased developmental rate of Rochelle-S on DAS-59122-7 with each generation of selection.

In York-US, there was no visible generational trend for change in the rate of larval development as a potential result of inbreeding depression or genetic drift that may have resulted from bottlenecking this colony each generation. In every generation, York-S on DAS-59122-7 produced more larvae in later instars compared to the corresponding York-US colony on DAS-59122-7 (Table 3). Tolerance in York-S was apparent after the first round of selection (F1). After 17 days, the percentage of first and second instars in York-US was 82.7 and 10.7% compared to 70.7 and 28.0% in York-S. After F1, tolerance of York-S to DAS-59122-7 appeared variable around an intermediate level. A high level or complete York-S resistance to DAS-59122-7 might have resulted in SSA results similar to York-US or York-S colony development on isoline (Table 4). Tolerance may have been greatest in the F3 generation where 85.3% of larvae were able to develop to third instar compared to the across-generation average of 53.3%. Tolerance in York-S is intermediate given the across generation mean number of larvae in third instar is 53.3% using DAS-59122-7 compared to 95.1 and 92.8% for York-US and York-S using isoline (Table 4).

Figure 1:
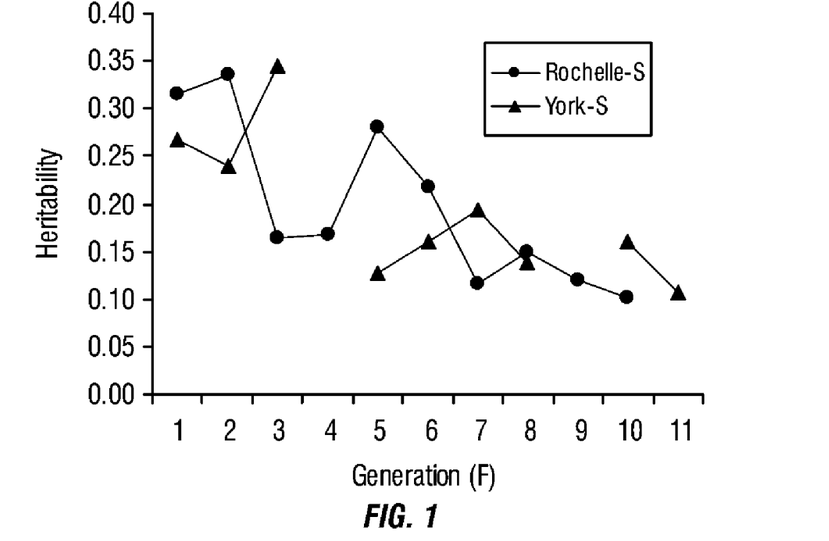
FIG. 1 shows realized heritability ($h^2$) of the survival characteristic over 10 and 11 generations of selection using DAS-59122-7 for Rochelle-S and York-S colonies, respectively.

Estimates of heritability ($h^2$) are presented for the Rochelle-S and York-S colonies in FIG. 1. Realized heritability was estimated at 0.31 and 0.27 for the F1 generation of Rochelle-S and York-S, respectively. After 10 and 11 generations, realized heritability was estimated at 0.10 and 0.11 for Rochelle-S and York-S, respectively (FIG. 1). There was an overall trend for a decline in realized heritability in both Rochelle-S and York-S with successive generations of selection and it appeared the largest reduction in variation occurred during the first few generations.

The impact of selection was detectible in the F1 generation of Rochelle-S. Survival rate of the F1 generation on DAS-59122-7 was 13% compared to the Rochelle-US across generation mean of 76.2% on isoline (Table 1). The percentage of females was lower in the Rochelle-S F1 generation compared to Rochelle-US and the Rochelle-S females were generally less fecund (Table 1). There were no apparent differences in fertility between F1 eggs of Rochelle-US and Rochelle-S colonies. Mean survival rate of the Rochelle-S colony increased gradually over the first five generations (Table 1). Survival rate in the F5 progeny was 15.9% or 5.1% higher than the across generation Rochelle-S mean (10.8%). After F1, estimates of percentage female, fecundity and fertility were variable around the across generation mean for each trait. There was no obvious across-generational trend in other life history traits measured for the Rochelle-S colony.

Similarly, the impact of selection was detectible in the F1 generation of York-S. Survival rate of the F1 generation on DAS-59122-7 was 0.4% compared to the York-US across generation mean of 82.7% on isoline maize (Table 1). The percentage of females was lower in the York-S F1 generation compared to York-US and York-S females were generally less fecund (Table 1). There was no apparent difference in fertility between F1 eggs of York-US and York-S colonies. Mean survival rate of the York-S colony was variable around an across generation mean of 10.3% (Table 1). Survival rate on DAS-59122-7 increased from 0.4 to 8.5% between the F1 and F2 generations; however 3 out of 9 subsequent generations resulted in survival rates less than 8.5% and the maximum survival rate was 23.4% in the F9 progeny. After F1, estimates of survival rate, percentage female, fecundity and fertility were variable around the York-S across-generation means for each trait. There was no obvious across generational trend in any adult life history traits measured for the York-S colony.

The root trainer experiment testing the injury potential of the F1 and F2 generations of Rochelle-S on DAS-59122-7 was repeated over 6 dates. When data were pooled from this experiment, there was a significant date by treatment interaction (F=3.4; df=15,54; P=0.0005) resulting from the mean node-injury score for the first date (0.11). This node-injury score represented 50% of the injury level observed for the other 5 dates (0.20-0.29). Data from the first date were then removed from the pooled analysis, resulting in a non-significant date effect (F=1.7; df=4.15; P=0.20) and date*treatment interaction (F=0.75; df=12.45; P=0.69). Across the 5 remaining dates, treatment had a significant effect on mean node-injury scores (F=233.7; df=3.12; P<0.0001). The mean node-injury score for Rochelle-US on isoline (0.76) was significantly greater than the other 3 treatments and indicated a moderate level of feeding pressure in this experiment (Table 5). There was no significant difference in mean node-injury scores between the F1 and F2 generations of Rochelle-S on DAS-59122-7 (Table 5). There was, however, a subtle numerical increase in mean node-injury measured for both the F1 and F2 generations of Rochelle-S on DAS-59122-7 compared to Rochelle-US on DAS-59122-7, but neither increase was statistically significant (Table 5). This subtle increase in injury potential to DAS-59122-7 was also evident in the consistency ratings, where the percentage of roots in the 0.26-0.50 node-injury category was 0% for Rochelle-US on DAS-59122-7 compared to 1.7 and 4.3% for the F1 and F2 generations of Rochelle-S, respectively. Table 5 illustrates the number of viable eggs infested per plant, mean node-injury ratings, node-injury scores per 100 viable eggs, and percentage of roots in 5 node-injury categories for greenhouse efficacy experiments characterizing the injury-potential of the Rochelle-S and Rochelle-US colonies on event DAS-59122-7 and nontransgenic isoline maize across generations of selection on DAS-59122-7.

The injury potential of Rochelle-S was evaluated in 2 additional large pot experiments; at generations F5 and F10 (Table 5). In both experiments, treatment had a significant effect on mean node-injury scores (F5: F=156.2; df=3.12; P<0.0001 and F10: F=64.2; df=3.12; P<0.0001). The mean node-injury scores for Rochelle-US on isoline (2.57 for F4 and 2.70 for F10) indicated a very high level of feeding pressure was achieved relative to the initial root trainer experiment (Table 5). Mean node-injury scores for the F5 and F10 generations of Rochelle-S on DAS-59122-7 were also significantly greater compared to the corresponding generations of Rochelle-US on DAS-59122-7. (Table 5). The mean node-injury score for Rochelle-S on isoline was significantly less than Rochelle-US on isoline at F5. However, at F10, Rochelle-S and Rochelle-US caused a similar amount of injury on isoline maize (Table 5).

TABLE 5

| Experiment[1] | Generation of selection | Insect colony | Maize hybrid | n | Viable eggs infested/ plant[2] | Mean ± SE node-injury rating[3] | Node-injury rating/100 eggs | Percentage of roots in each node-injury category | | | | |
|---|---|---|---|---|---|---|---|---|---|---|---|---|
| | | | | | | | | 0.00-0.25 | 0.26-0.50 | 0.51-0.99 | 1.00-1.99 | 2.00-3.00 |
| Trainer | F1 | Rochelle-S | 59122 | 115 | 39 | 0.07 ± 0.020 a | 0.18 | 98.3 | 1.7 | 0 | 0 | 0 |
| | F2 | Rochelle-S | 59122 | 117 | 41 | 0.08 ± 0.019 a | 0.19 | 95.7 | 4.3 | 0 | 0 | 0 |

TABLE 5-continued

| Experiment[1] | Generation of selection | Insect colony | Maize hybrid | n | Viable eggs infested/ plant[2] | Mean ± SE node-injury rating[3] | Node-injury rating/100 eggs | Percentage of roots in each node-injury category | | | | |
|---|---|---|---|---|---|---|---|---|---|---|---|---|
| | | | | | | | | 0.00-0.25 | 0.26-0.50 | 0.51-0.99 | 1.00-1.99 | 2.00-3.00 |
| | F2 | Rochelle-US | 59122 | 112 | 41 | 0.03 ± 0.020 a | 0.07 | 100 | 0 | 0 | 0 | 0 |
| | F2 | Rochelle-US | Isoline | 119 | 41 | 0.76 ± 0.019 b | 1.85 | 16.8 | 14.3 | 24.4 | 43.7 | 0.8 |
| Pot 1 | F5 | Rochelle-S | 59122 | 49 | 484 | 0.85 ± 0.091 a | 0.18 | 26.5 | 18.4 | 18.4 | 24.5 | 12.2 |
| | F4 | Rochelle-US | 59122 | 50 | 470 | 0.10 ± 0.090 b | 0.02 | 94 | 4 | 2 | 0 | 0 |
| | F5 | Rochelle-S | Isoline | 50 | 484 | 2.29 ± 0.090 c | 0.47 | 2 | 2 | 4 | 16 | 76 |
| | F4 | Rochelle-US | Isoline | 50 | 470 | 2.57 ± 0.090 d | 0.55 | 2 | 2 | 2 | 8 | 86 |
| Pot 2 | F10 | Rochelle-S | 59122 | 30 | 726 | 1.83 ± 0.102 a | 0.25 | 6.7 | 3.3 | 13.3 | 26.7 | 50 |
| | F10 | Rochelle-US | 59122 | 30 | 804 | 0.19 ± 0.102 b | 0.02 | 79.9 | 6.7 | 6.7 | 6.7 | 0 |
| | F10 | Rochelle-S | Isoline | 30 | 726 | 2.89 ± 0.102 c | 0.40 | 0 | 0 | 0 | 3.3 | 96.7 |
| | F10 | Rochelle-US | Isoline | 30 | 804 | 2.70 ± 0.102 c | 0.34 | 3.3 | 0 | 0 | 0 | 96.7 |

Within each experiment, means followed by the same lower-case letter are not significantly different at $P \leq 0.05$ (t-test).
[1]Three greenhouse efficacy experiments were conducted using either a root trainer or large pot test system.
[2]Plants in the trainer experiment infested with 100 eggs 13 days after planting. Plants in the Pot 1 experiment infested with 400 and 1,000 eggs 17 and 24 days after planting (1,400 eggs total). Plants in the Pot 2 experiment infested with 600 eggs 14 and 20 days after planting (1,200 eggs total). Hatch tests were used to estimate number of viable eggs infested.
[3]Roots were visually scored for injury using the 0-3 node-injury scale (Oleson et al. 2005). Roots scored 32 days after planting in the trainer experiment, 59 days after planting in the Pot 1 experiment, and 60 days after planting in the Pot 2 experiment.

A similar change in injury potential was measured for the F1 and F2 generations of York-S on DAS-59122-7 in the large pot test system. In this experiment, treatment also had a significant effect on mean node-injury scores (F=18.2; df=3.12; P<0.0001). Table 6 describes the number of viable eggs infested per plant, mean node-injury ratings, node-injury scores per 100 viable eggs, and percentage of roots in 5 node-injury categories for greenhouse efficacy experiments characterizing the injury-potential of the York-S and York-US colonies on DAS-59122-7 and nontransgenic isoline maize across generations of selection on DAS-59122-7. The mean node-injury score for York-US on isoline (0.62) was significantly greater than the other 3 treatments and indicated a moderate level of feeding pressure in this experiment (Table 6). There was no significant difference in mean node-injury scores between York-S F1 and F2 (Table 6). However, both the F1 and F2 generations caused significantly more root injury to DAS-59122-7 compared to York-US on DAS-59122-7 (Table 6). However, at F10, Rochelle-S and Rochelle-US caused a similar amount of injury on isoline maize (Table 5). This significant increase in injury potential after 1 and 2 generations of selection was also evident in the consistency ratings, where the percentage of roots in each node-injury category shifted to higher categories with each additional generation of selection (Table 6).

The injury response for York-S at generations F6 and F11 was nearly identical to that observed for Rochelle-S at generations F5 and F10. In the experiments evaluating York-S F6 and F11, treatment had a significant effect on mean node-injury scores (F6: F=147.9; df=3.12; P<0.0001 and F11: F=179.2; df=3.12; P<0.0001). Mean node-injury scores for the F6 and F11 generations of York-S on DAS-59122-7 were also significantly higher than the corresponding F4 and F10 York-US scores on DAS-59122-7 (Table 6). The mean node-injury score for York-S F6 on isoline was significantly greater than York-US F4 on isoline at F5. However, at F11, Rochelle-S and Rochelle-US caused a similar amount of injury on isoline maize (Table 5).

TABLE 6

| Experiment[1] | Generation of selection | Insect colony | Maize hybrid | n | Viable eggs infested/ plant[2] | Mean ± SE node-injury rating[3] | Node-injury rating/100 eggs | Percentage of roots in each node-injury category | | | | |
|---|---|---|---|---|---|---|---|---|---|---|---|---|
| | | | | | | | | 0.00-0.25 | 0.26-0.50 | 0.51-0.99 | 1.00-1.99 | 2.00-3.00 |
| Pot 3 | F1 | York-S | 59122 | 55 | 136 | 0.11 ± 0.031 a | 0.08 | 89.1 | 7.3 | 3.6 | 0 | 0 |
| | F2 | York-S | 59122 | 45 | 134 | 0.19 ± 0.035 a | 0.14 | 75.6 | 11.1 | 11.1 | 2.2 | 0 |
| | F1 | York-US | 59122 | 55 | 144 | 0.01 ± 0.031 b | 0.01 | 100 | 0 | 0 | 0 | 0 |
| | F1 | York-US | Isoline | 55 | 144 | 0.62 ± 0.031 c | 0.43 | 29.1 | 14.5 | 29.1 | 27.3 | 0 |
| Pot 4 | F6 | York-S | 59122 | 50 | 622 | 0.52 ± 0.077 a | 0.08 | 36 | 28 | 10 | 26 | 0 |
| | F4 | York-US | 59122 | 50 | 429 | 0.03 ± 0.077 b | 0.01 | 50 | 0 | 0 | 0 | 0 |
| | F6 | York-S | Isoline | 50 | 622 | 2.37 ± 0.077 c | 0.38 | 2 | 0 | 0 | 20 | 78 |
| | F4 | York-US | Isoline | 50 | 429 | 1.02 ± 0.077 d | 0.24 | 20 | 16 | 12 | 34 | 18 |
| Pot 5 | F11 | York-S | 59122 | 30 | 726 | 2.07 ± 0.109 a | 0.28 | 3.3 | 6.7 | 10 | 23.3 | 56.7 |
| | F10 | York-US | 59122 | 30 | 756 | 0.13 ± 0.109 b | 0.02 | 86.6 | 6.7 | 6.7 | 0 | 0 |
| | F11 | York-S | Isoline | 30 | 726 | 2.85 ± 0.109 c | 0.39 | 0 | 0 | 0 | 3.3 | 96.7 |
| | F10 | York-US | Isoline | 30 | 756 | 2.89 ± 0.109 c | 0.38 | 0 | 0 | 0 | 0 | 100 |

Within each experiment, means followed by the same lower-case letter are not significantly different at $P \leq 0.05$ (t-test).
[1]Three greenhouse efficacy experiments were conducted using a large pot test system.
[2]Plants in the Pot 3 experiment infested with 100 eggs 13, 19, and 28 days after planting (300 eggs total). Plants in the Pot 4 experiment infested with 400 and 1,000 eggs 17 and 24 days after planting (1,400 eggs total). Plants in the Pot 5 experiment were infested with 600 eggs 14 and 20 days after planting (1,200 eggs total). Hatch tests were used to estimate number of viable eggs infested.
[3]Roots were visually scored for injury using the 0-3 node-injury scale (Oleson et al. 2005). Roots scored 74 days after planting in the Pot 3 experiment, 59 days after planting in the Pot 4 experiment, and 60 days after planting in the Pot 5 experiment.

The mean node-injury score per 100 viable eggs was calculated for each treatment across experiments to better facilitate comparison of injury potential to DAS-59122-7 across generations of selection. This metric does not account for intraspecific competition effects; however, it does allow for a normalized comparison of injury potential across experiments with different rates WCR egg infestation. For both unselected colonies, the mean node-injury score per 100 viable eggs on DAS-59122-7 remained consistently low across generations, ranging from 0.01 to 0.07 (less than 1 root pruned) (Tables 5 and 6). For Rochelle-S, the mean node-injury score per 100 viable eggs on DAS-59122-7 was 0.18, 0.19, 0.18, and 0.25 for generations F1, F2, F5, and F10, respectively (Table 5). A similar response was observed for York-S on DAS-59122-7 across generations, where the mean node-injury score per 100 viable eggs on DAS-59122-7 was 0.08, 0.14, 0.08, and 0.28 for generations F1, F2, F6 and F11 (Table 6). Results from both selected colonies indicate that survivors from the first generation of selection have a slight increase in injury potential and that repeated generations of selection on DAS-59122-7 without random mating resulted in a gradual increase in the injury potential to DAS-59122-7.

It is noteworthy that these colonies exhibit tolerance, rather than complete resistance, to event DAS-59122-7. In this respect, the development of the colonies has already provided valuable information, namely that a single gene that is responsible for complete resistance to DAS-59122-7 is rare in wild populations, that a heritable characteristic conferring tolerance to DAS-59122-7 is present in wild populations, that this heritable characteristic is not a realistic threat to the durability of DAS-59122-7 efficacy. Instead, based on these data, a more complex genetic basis for intermediate tolerance to DAS-59122-7 is apparently present in WCR populations, with expression of one or multiple genes resulting in intermediate tolerance to the event. Tolerance was heritable, and results from consecutive generations of the selection show the tolerance is variable around an intermediate level, the incidence of these partial resistance gene or genes appears variable but stable over several generations of selection without random mating, thereby resulting in variable levels of tolerance and larval injury potential to DAS-59122-7 maize over several generations.

The knowledge that a major resistance gene in WCR to DAS-59122-7 is rare in wild populations presents several opportunities for investigation and use of colonies tolerant to the event.

One potential use is in the realm of negative cross-resistance (NCR). The current generation of pesticides includes toxins isolated from bacterial broths, such as Spinosad, and transgenic plants containing genes that code for an insecticidal protein. It is highly likely that in some cases target-site insensitivity to these new classes of insecticides occur in the pest insects. Target-site insensitivity is a major mechanism of resistance to second generation pesticides. After deploying these novel toxins, it is likely that a single (or multiple) point mutation in the gene coding for the target site in the insect's gut or other target system results in the insects developing field resistance. Additionally, metabolic resistance may occur where the insects have a greater ability to alter the toxin such that it has reduced toxic activity.

Even if metabolic resistance occurs to such resistance factors, the metabolic resistance does not rule out the possibility of developing NCR compounds for control of metabolic insecticide resistance.

In spite of the lack of large-scale screening for NCR toxins, there still has been discovery of such compounds. For example, a NCR factor to aphids has been identified that was resistant to insecticides through increased production of a carboxylesterase, E4.

Although NCR factors do occur within classes of toxins, there is no distinct reason to believe that NCR factors will only be found in the same class of compounds as the first toxin. Although compounds within the classes of toxins appear to be a logical starting place, exemplary screens for NCR toxins involve random screens for compounds. The random screens are, in one embodiment, coupled with a "clue-based" screen.

An advantage of random screening for NCR factors is that an understanding of the molecular basis of resistance is not necessary for the development of the second compound. Knowledge on the molecular basis of resistance typically lags years behind the first appearance of tolerant insects in the field. However, knowing the basis of tolerance is helpful for 'clue-based' screening. But if discovery of the molecular basis of pesticide tolerance is too costly or time consuming, one may be able to use the tolerant line (or lines) in a random screen for NCR factors.

Tests using tolerant and susceptible lines of insects are easily integrated into current large-scale automated screening methodologies. The screens identify compounds that are toxic to the tolerant line (or lines) in the bioassay and not toxic to the insect lines that are susceptible to the already commercialized toxin.

Ordinarily when seeking negative cross-resistance in pest control compounds, the mechanism of resistance is based on a single gene, meaning a homozygous resistant strain (R/R) is evaluated with a number of potentially toxic molecules, e.g., natural molecules, synthetic molecules, chemicals, compounds, biotechnical species, and biotechnical moieties, to determine a second toxin that is more toxic to the resistant strain (R/R) than to the susceptible strain (S/S). The toxic molecules include variants, mutants, metabolites, and derivatives. A susceptible control strain (S/S) is also evaluated with the same compounds. Exemplary chemicals include a) *Bacillus thuringiensis* proteins and their variants, b) clorinated hydrocarbons, c) organophosphates, d) pyrethroids, e) carbamates, f) variants of toxins from the bacteria *Photorhabdus luminescens*, g) insect growth regulators and their derivatives, h) alpha-amylase inhibitors, i) lectins, j) Spinosad derivatives, k) spinosyns and their derivatives, l) derivatives of insecticidal compounds from the bacteria *Saccharopolyspora spinosa*, m) *Bacillus thuringiensis* strains and their variants, n) protease inhibitors and their derivatives, o) Cysteine protease inhibitors and their derivatives, p) Bowman-Birk Inhibitors and their derivatives, q) Kunitz inhibitors and their derivatives, r) *Saccharopolyspora spinosa* strains and derivatives of their insecticidal and non-insecticidal toxins, and s) imidacloprid or derivatives of imidacloprid.

Molecules may be supplied from randomly or selectively generated chemicals, and random or selective (chemical rationale approach) screening of chemicals. The molecules to be evaluated further include molecules supplied from bioprospecting from plant, animal, bacteria, and fungal organisms or extracts of these organisms and from prokaryotic or eukaryotic organisms. The molecules to be evaluated also include molecules supplied from the generation of antibodies showing preference for binding to proteins or protein complexes or membranes in the organism involved in negative cross-tolerance (binding preference for versions of the protein that are resistant to the first toxin) and generation of random peptide libraries and bio-panning using phage display. A random peptide library is made and is screened for affinity to the product of the target of interest, e.g., the gene product of the target site. The resistant allele, more specifically the protein product, is then used to identify a protein that has high affinity to the gene product to generate a NCR toxin for specifically targeting the resistant insect. The molecules to be evaluated also include molecules obtained from combinatorial shape libraries and molecules supplied using combinatorial chemistry. Those compounds that are more toxic to the resistant strain than to the susceptible strain are considered to be positive compounds for the initial evaluation.

A heterozygous strain (R/S) of the target population is evaluated with the positive compounds to test their effectiveness against the heterozygous insects. Thus, the resistant (R/R) and susceptible (S/S) insects are crossed and the progeny bio-assayed against the new toxin. It should be determined whether tolerance is sex-linked, since if the tolerance is sex-linked, individuals of the proper sex that carry two alleles of the gene should be used. The heterozygotes are screened by using separate applications of the first toxin and the positive compound being tested, i.e., the second toxin, to determine if separate applications of the first toxin and the second toxin are at least as toxic to the heterozygous strain (R/S) as to the susceptible strain (S/S) of the target population.

If the heterozygotes are killed by separate applications of the first toxin and the positive compound being tested, the positive compound is given a high priority for development and commercial exploitation. A high negative cross-tolerance priority is assigned to the second toxin if separate applications of the first toxin and the second toxin are at least as toxic to the heterozygous strain (R/S) as to the susceptible strain (S/S). Thus, based on the toxicity of the compound to heterozygous individuals, the practical applicability of each toxin is prioritized and the compounds capable of killing the heterozygotes receive a high priority while those compounds that only impact homozygous individuals are subjected to further testing and evaluation to determine their prioritization. The priority compounds, in one embodiment, are prioritized for advancement to additional evaluations which are utilized to make commercial development prioritization decisions. In an alternative embodiment, the high priority compounds receive a commercialization prioritization.

The heterozygous strain is evaluated with the first toxin and the second toxin applied at the same time to determine if the application of the first toxin and the second toxin at the same time is at least as toxic to the heterozygous strain (R/S) as to the susceptible strain (S/S). If the application of the first toxin and the second toxin at the same time is not at least as toxic to the heterozygous strain as to the susceptible strain, the compound is given a low priority for further development.

In the case of insects tolerant to DAS-59122-7, including but not limited to the York and Rochelle colonies, however, the mechanism of resistance appears to be more complex. As noted above, based on the data produced during selection of the tolerant colonies, it appears that this tolerance to event DAS-59122-7 is not a simple gene model where a single recessive gene with two alleles confers resistance to the event. Rather, this mechanism of tolerance to DAS-59122-7 appears to be a more complex genetic system comprising multiple genes. This is because despite many generations of selection for tolerant organisms, the tolerant strains still do not exhibit complete or near-complete resistance to the event. This is in contrast to the mechanism of resistance for most other known pesticides and herbicides, where frequently a mutation at a single gene is sufficient to confer resistance.

The nature of the tolerance to DAS-59122-7, therefore, presents additional opportunities in the context of insect resistance management. For example, while ordinarily negative cross-resistance is a binary situation (either an organism has resistance, and therefore negative cross-resistance, or it does not), with the more complex tolerance genetics of resistance to DAS-59122-7, there are potentially a greater number of possible negative cross-resistance situations. This is because a rootworm that has greater susceptibility to DAS-59122-7 may, depending on the basis of the additional susceptibility, have increased susceptibility to one or more other toxins. Given that there are multiple genes for which negative cross-resistance (or tolerance) may be associated, it is possible for many negative cross-resistant compounds to either exist currently or be engineered based on the mechanism of tolerance to DAS-59122-7.

Once a pair of NCR factors is determined, many different types of applications of the toxins to the insects can be used. For example, both toxins can be applied at the same time every time, one of the toxins can be applied on an intermittent basis, both toxins can be applied on an intermittent basis, and the toxins can be applied in an alternating type application. In one embodiment, the toxins are delivered to the target population utilizing at least one of sprays, pellets, powders, baited or non-baited traps, and transgenic organisms. For example, in the case of western corn rootworm, a first compound is introduced to the field by spraying the compound on the field, incorporating the compound via transgenic crops, or any other method known in the art. In the context of DAS-59122-7, typically transgenic corn incorporating that event will be combined with another form of pesticide, whether it be chemical, transgenic, or some other form. If resistant forms exist in the particular field, a second compound is then applied to the field. In addition, transgenic antibodies or antibody conjugates with toxins attached could be used in the selection assays. Thus, in one embodiment, the above-described method is used to manage a tract of land against a resistant strain of a target population. In an alternative embodiment, the above described method is used as part of a pest management system to manage a pest population.

Further detail regarding methods for screening for negative cross-tolerance may be found in PCT Publication WO 01/92561 A2, herein incorporated by reference in its entirety. In addition to usefulness and negative cross-tolerance development strategies, the colonies of the present invention are also useful in understanding the mechanism of western corn rootworm tolerance to various insect control strategies. The resistant colonies may be compared to wild type colonies lacking such tolerance or containing such tolerance at lower frequencies to determine genetic and/or phenotypic differences between such insects, thereby assisting in identification of the tolerance mechanism in the selected colonies.

This has the potential to be particularly helpful given the complex genetic nature of tolerance to DAS-59122-7. Genetic comparisons between the tolerant colonies disclosed herein and susceptible or wild type WCR colonies will yield valuable information about both the nature of the DAS-59122-7 event itself as well as the mechanism by which insects build tolerance to the event. This type of analysis may be done by any number of methods known in the art.

Further, these colonies may be used to determine whether positive cross-tolerance exists with any currently-existing corn rootworm control tactics. For example, the selected colonies may be exposed to maize plants exhibiting transgenic events such as MON863, Cry3Aa, other Cry proteins, or chemical insecticides, to determine whether positive cross-tolerance exists. In addition to determining whether such cross-tolerance exists, it will also help determine the potential for, and estimated rate of, field development of tolerance to event DAS-59122-7.

Another opportunity in the context of resistance management is using the tolerance traits identified via the York and Rochelle selected colonies as part of a resistance management strategy protecting against recessive traits conferring resistance or tolerance levels greater than the characteristics of the York or Rochelle selected colonies. The most frequently-used current IRM strategy is exposing insects to a high dose of a pest control substance and the planting of a refuge (a portion of the total acreage using seed lacking a gene conferring pest resistance), as it is commonly-believed that this will delay the development of insect resistance to resistant crops by maintaining insect susceptibility. The high dose/refuge strategy assumes that resistance is recessive and is conferred by a single locus with two alleles resulting in three genotypes: susceptible homozygotes (SS), heterozygotes (RS), and resistant homozygotes (RR). It also assumes that there will be a low initial resistance allele frequency and that there will be extensive random mating between resistant and susceptible adults. Under ideal circumstances, only rare RR individuals will survive a high dose produced by the resistant crop or otherwise exposed to the pests. Both SS and RS individuals will be susceptible to the given toxin. A structured refuge is a non-pesticidal portion of a grower's field or set of fields that provides for the production of susceptible (SS) insects that may randomly mate with rare resistant (RR) insects surviving the pesticidal crop to produce susceptible RS heterozygotes that will be killed by the pesticidal crop. This will remove resistant (R) alleles from the insect populations and delay the evolution of resistance.

The high dose/refuge strategy is the currently-preferred strategy for IRM. Non-high dose strategies are currently used in an IRM strategy by increasing refuge size. The refuge is increased because lack of a high dose could allow partially resistant (i.e., heterozygous insects with one resistance allele) to survive, thus increasing the frequency of resistance genes in an insect population. For this reason, numerous IRM researchers and expert groups have concurred that non-high dose expression of insecticidal traits presents a substantial resistance risk relative to high dose expression. However, such non-high dose strategies are typically unacceptable for the farmer, as the greater refuge size leaves a larger proportion of the crop at risk to greater pest damage and further loss of yield.

Currently, the size, placement, and management of the refuge is often considered critical to the success of the high dose/structured refuge strategy to mitigate insect resistance to the Bt proteins produced in corn, cotton, and potatoes. Structured refuges are generally required to include all suitable non-pesticidal host plants for a targeted pest that are planted and managed by people. These refuges could be planted to offer refuges at the same time when the resistant crops are available to the pests or at times when the resistant crops are not available. The problems with these types of refuges include ensuring compliance with the requirements by individual farmers. Because of increased pest pressure and the decrease in yield in refuge planting areas, some farmers choose to eschew the refuge requirements, and others do not follow the size and/or placement requirements. These non-compliance issues result in either no refuge or less effective refuge, and a corresponding increase in the development of resistant pests.

A prominent hypothesis is that minor insecticide resistance or tolerance genes can accelerate pest adaptation via major resistance genes. This has been referred to as coadaptation; where selection and integration of resistance genes with other loci ameliorate the deleterious effects of resistance. The general theory goes that increased pest survival from a minor gene creates a means by which rare major resistance genes escape selection and thereby increase in frequency. This hypothesis is based mostly on the early work using pest exposure to synthetic organic insecticides. A classic example of this interaction is the PEN—a gene, which slows cuticular penetration of synthetic insecticides in houseflies. In this instance, houseflies developed resistance based on a (minor) cuticle gene and not a major putative resistance gene that metabolizes the toxin or confers a receptor-mediated resistance etc. More recently, laboratory selection experiments have been used to study the interactions between polygenic "minor" and monogenic "major" genes for pest resistance. In laboratory selection experiments, the rate of insect exposure to insecticides are often reduced well below field exposure rates. This scenario facilitates experiments with small populations that may be otherwise killed by exposure to field rates of insecticide. In laboratory experiments, tolerant or resistant phenotypes frequently result from polygenic traits, compared to monogenic traits identified in the same species where selection in the field occurs at significantly higher rates. The precision with which laboratory selection results can be extrapolated to field conditions is discussed by Groeters and Tabashnik (2000). They use an analysis of literature-based data along with a simulation model to test hypotheses on whether the method of selection biases selection experiment results toward major or minor genes. They found little association between the type of selection method and whether the method yielded major or minor resistance genes. Results of their simulation modeling showed the effectiveness of refuge was related more to the intensity of selection and less to whether resistance was considered major or minor. They conclude that understanding selection intensity is more important than understanding the number and relative contribution of resistance loci. A much less popular hypothesis is that minor or polygenic resistance traits can interfere with pest adaptation via major monogenic resistance. Lande (1983) describes how pest adaptation via a major resistance gene (monogenic mutation) can be prevented or delayed by a minor (polygenic mutation) resistance gene despite strong selection pressure; rarity of major resistance is an essential condition for this interaction.

This interaction may be present in the DAS-59122-7 maize and corn rootworm system and could have a large and beneficial effect on the durability of DAS-59122-7 maize. The characteristic identified in the York and Rochelle selected colonies creates resistance management opportunity in that rootworms possessing these genes conferring tolerance, without conferring complete or major resistance, can act as refuge insects. As a result, crops incorporating DAS-59122-7 should be able to be planted with little or no refuge plants for rootworms, as the nature of the development of resistance to the event is contrary to the traditionally-believed resistance paradigm.

The potential effectiveness of this resistance management strategy is illustrated by FIG. 2. In FIG. 2, as described previously, the expected development of resistance to DAS-59122-7 is indicated by the lines, given either a 0.0005 or 0.001 incidence of a resistance allele present in the wild. As can be seen from the data from generations of selection of the York and Rochelle tolerant colonies, resistance has not developed according to the predicted timeframe. Instead, a low level of tolerance to DAS-59122-7 has developed over the course of generations, and has varied somewhat as opposed to steadily increased. This is consistent with a polygenic tolerance mechanism, where certain genes contributing to tolerance are lost from one generation to the next due to various genetic events, such as crossing over or mutations.

Several factors associated with the selection materials and methods increase the inferential power of findings from this study. First, the selection likely included a large degree of existing additive genetic variation for DAS-59122-7 tolerance. Each founding population of WCR originated with 1,000 wild males. The work of Kim et al. (2007) suggests that there was very little loss of genetic diversity by introgressing a non-diapause trait into the Rochelle, Ill. and York, Nebr. founding populations. In a genetic analysis of several diapausing and one non-diapausing laboratory colonies, they found relatively low genetic diversity among nine diapausing colonies that had been reared for approximately 0-22 generations and only a moderate loss of genetic diversity in the non-diapausing colony that had been reared for approximately 190 generations. Although Rochelle, Ill. and York, Nebr. are separated by approximately 800 km, results from this study suggest there was a similar degree of additive genetic variation for tolerance to DAS-59122-7 in both Rochelle, Ill. and York, Nebr. founding populations. These results corroborate the earlier work using microsatellite markers to study genetic variation in rootworm populations from Kansas to the east coast of the US, which concluded there was high genetic similarity in WCR over much of the US and that no obvious genetic structuring had resulted since the eastward expansion of this pest. As a result, the information gleaned from these experiments and data is more broadly applicable to US WCR populations and not specific to the regions surrounding Rochelle, Ill. or York, Nebr., and strategies developed from this information have broader applicability.

Further, the method of selection was ecologically relevant. Larval exposure to insecticidal proteins in the roots of maize is complex over space and time, and root-tissue function is the primary explanation for variation in total protein. For example, the growing point is metabolically active, undergoing rapid cell division, protected by mucilage and relatively rich in total soluble protein compared to more distal tissue that has mostly structural and vascular functions. The relative quantity and distribution of insecticidal protein made by DAS-59122-7 follows the pattern of total soluble protein in maize roots. Consequently, using DAS-59122-7 as a means of selection increased the likelihood of integrating realistic plant and larval interactions resulting when exposure is complex. Moreover, similarity between the F1 survival rates of 0.4 to 1.3%, using seedlings and laboratory conditions, and the field estimates of 0.6 to 4.0% reported by Storer et al. (2006) shows there was a high degree of ecological relevance in the selection method. The fact that these data represent a closer approximation to actual field conditions as compared to direct-exposure studies also support the more general applicability of data obtained from these tolerant colonies, as well as the resistance management strategies and other information that can be derived from the tolerant insects.

It can be concluded from this resistance risk assessment that putative or major resistance to DAS-59122-7 is rare in US populations of western corn rootworm. Increased confidence comes from the large size of initial collections relative to the known genetic diversity in rootworm populations and the ecological relevance of the selection method. Survival of rootworms on DAS-59122-7 in the laboratory and the field is very low and variable across locations and years. It can be concluded that much of the rootworm survival on DAS-59122-7 is heritable and inheritance of the apparently polygenic tolerance trait is complex. This tolerance trait is considered minor as it relates to the efficacy of DAS-59122-7.

As can be seen from these data, even with no refuge insects to dilute the presence of genes conferring resistance or tolerance to DAS-59122-7, the York and Rochelle selected colonies had not developed putative resistance to the event, even after at least 10 generations of selection. As also can be seen from these data, WCR that survive DAS-59122-7 have a heritable trait or traits that appear independent of a theoretical major single gene for resistance to DAS-59122-7 with recessive inheritance. Consequently, insects with this characteristic identified in Rochelle and York selected colonies can serve as refuge for major resistance genes for other pest management strategies. Given these data, plants incorporating DAS-59122-7 should not need a structured refuge in order to prevent resistance to the event from developing, or at a minimum, a drastically reduced refuge (as compared to the currently-accepted 20%) may be used. For example, plants incorporating DAS-59122-7 may comprise 85%, 86%, 87%, 88%, 89%, 90%, 91%, 92%, 93%, 94%, 95%, 96%, 97%, 98%, 99%, 99.5%, or even 100% of the plants intended to be in a given plot. Of course, low levels of off-type seeds can occur normally during commercial hybrid seed production, so a plot will rarely, if ever, actually have 100% of its plants incorporating event DAS-59122-7. As a result, a plot may be considered to have 100% of its plants incorporating this event even if some low level of seeds not containing event DAS-59122-7 are present.

The ability to reduce or eliminate structured refuge for this event will result in an increase in crops protected from rootworm infestation by DAS-59122-7, produce a substantial pool of susceptible rootworms to delay major gene resistance, and accordingly increased yields for growers. It also reduces or eliminates the issues regarding compliance that are inherent whenever a structured refuge is required. As a result, a grower could have the entirety of a given crop protected with DAS-59122-7 to deter rootworms, as well as an additional 80% of the crop (or whatever percentage is required from a regulatory perspective) protected with an alternative pest management strategy, such as chemical pesticide, another transgenic event, or any other pest management method, in order to improve control of rootworms further while still maintaining the commonly-used structured refuge for the second pest management strategy.

Simulation data supports the empirical data described above, namely that a tolerance trait can produce sufficient refuge insects to delay the development of resistant insects. A simple population genetics model of Diabrotica in a landscape of continuous corn was used to explain how the tolerance trait(s) can act as an adaptive barrier or slow the development of resistance based on major resistance genes. Two autosomal, di-allelic, genes are modeled: a minor (tolerance) gene designated with X for wild type and Y for tolerance; and a major gene designated with A for wild type and B for resistance, with a maximum survival of 1.0 on toxic corn. For the purpose of this simulation model, rootworm tolerance to event DAS-59122-7 was assumed to be a single gene and parameter estimates for this gene were derived from the biological response of the surviving phenotype reported in Lefko et al. (2008), which is incorporated by reference herein in its entirety. To study the interaction between the tolerance trait and putative resistance; WCR adaptation to DAS-59122-7 was first modeled without the tolerance trait or Y allele. We excluded the Y allele, used off-type seeds at a proportion 0.0075 and no structured refuge. We define off-types here as seeds not containing DAS-59122-7. Results of this simulation are presented in FIG. 3.

Figure 3:
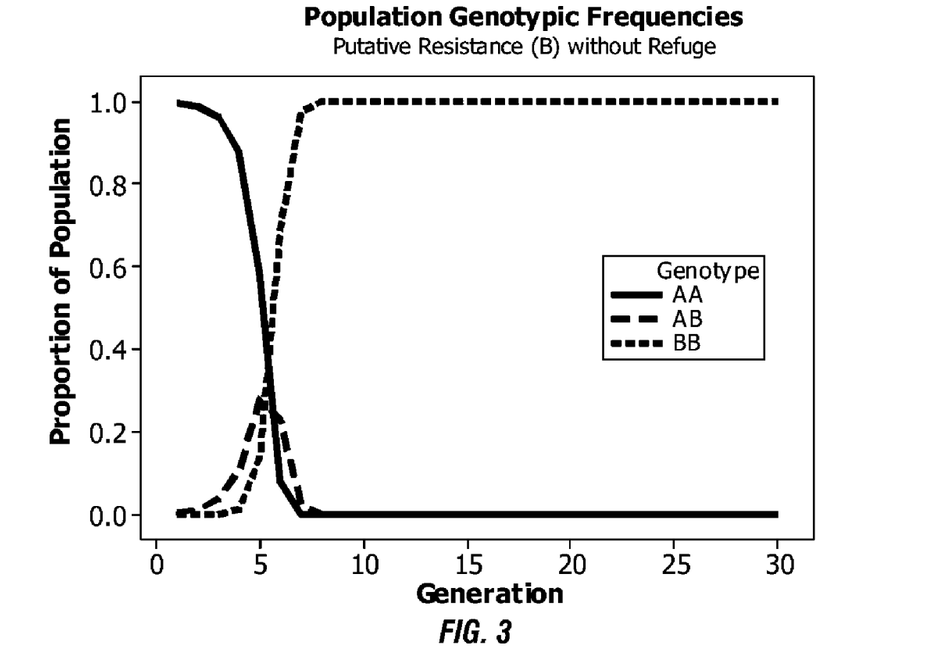
FIG. 3 shows population genotypic frequencies over generations using the WCR benchmark simulation excluding the tolerance trait (Y), and excluding any block or blended refuge.

Putative resistance developed rapidly with the proportion of heterozygous (AB) individuals peaking at 0.3 after 5 generations and homozygous (BB) individuals exceeding 0.5 after 6 generations (FIG. 3). The line predicting the increase in the proportion of homozygous (BB) resistant individuals was very steep with 0.69 of the population homozygous for B in 6 generations and reaching 0.99 in 8 generations.

Figure 4:
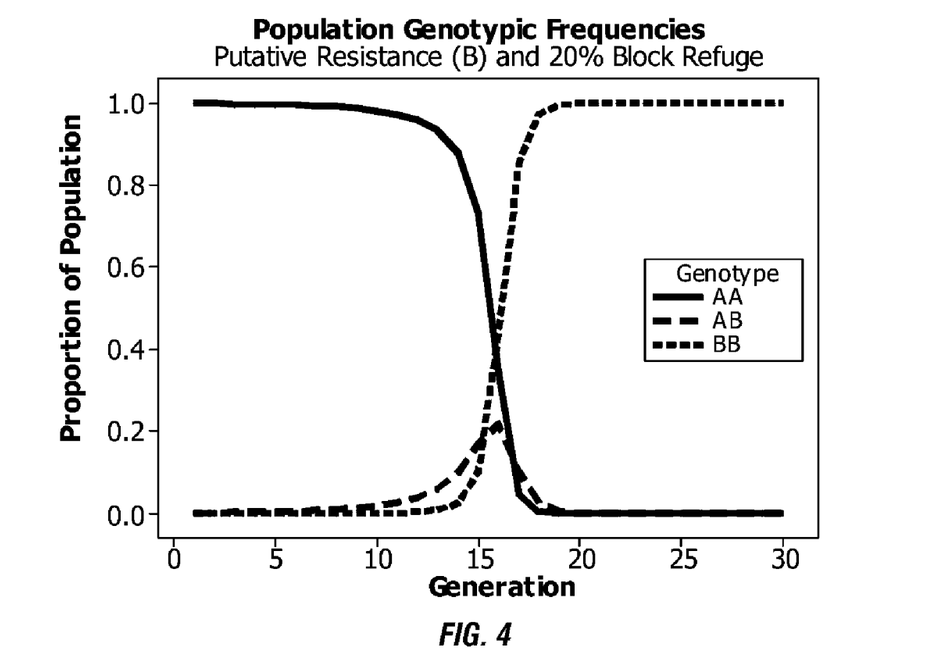
FIG. 4 shows population genotypic frequencies over generations using the WCR benchmark simulation excluding the tolerance trait (Y) and including a block refuge at a proportion of 0.20.
Figure 5:
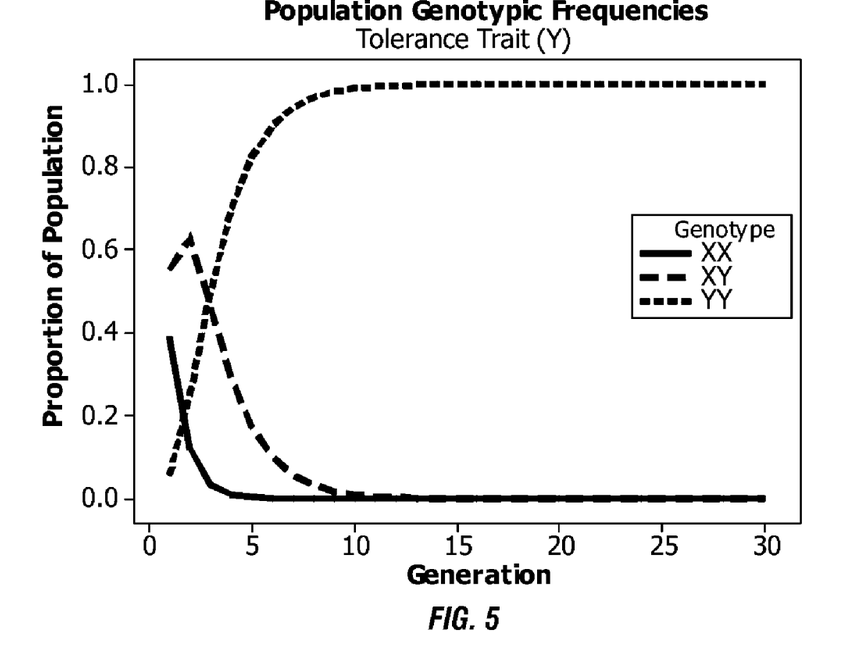
FIG. 5 shows population genotypic frequencies over generations using the WCR benchmark simulation excluding the putative resistance gene (B), and excluding any block or blended refuge.

The effect of a 20% structured adjacent block refuge excluding the Y allele (FIG. 4) and using the same parameters as used in FIG. 3 was then simulated. This simulation exemplifies the currently-accepted resistance management strategy for events with putative or major resistance gene(s). The relative impact of the 20% block refuge was large; it delayed the onset of ≧0.5 B allele frequency by roughly 2.5 times with the heterozygous (AB) proportion of the population peaking at 0.21 after 16 generations and the homozygote proportion reaching 0.85 after 17 generations. The line predicting the proportion of homozygous resistant (BB) individuals was still very steep with the proportion of BB individuals reaching 0.99 after 19 generations. Fixation of B occurred by the 22nd generation (FIG. 4) Next, we modeled the Y allele in the absence of both a putative or major resistance gene and any structured refuge. The same off-type seed rate of 0.0075 was used. Parameterization for the Y allele was derived from the study using selected colonies to investigate resistance risk in survivors of DAS-59122-7 (Lefko et al. 2008). The Y allele was assumed to be relatively frequent and additive in its inheritance. Despite having a maximum YY survival rate of 0.2, the Y allele increased in frequency very rapidly (FIG. 5). The proportion of the population responding to Y mimicked the response observed by Lefko et al. (2008), where the largest changes in both colonies selected for survival occurred after the first two generations. The proportion of XY individuals peaked at 0.6 by the 2nd generation and 0.5 were YY by the 3rd generation (FIG. 5). The line predicting the proportion of individuals homozygous for Y was not as steep as the line predicting the proportion of BB individuals when B was modeled independently. The proportion of YY individuals was 0.90 after 7 generations and 0.99 after 10 generations. Fixation of Y allele occurred by the 19th generation.

Figure 6:
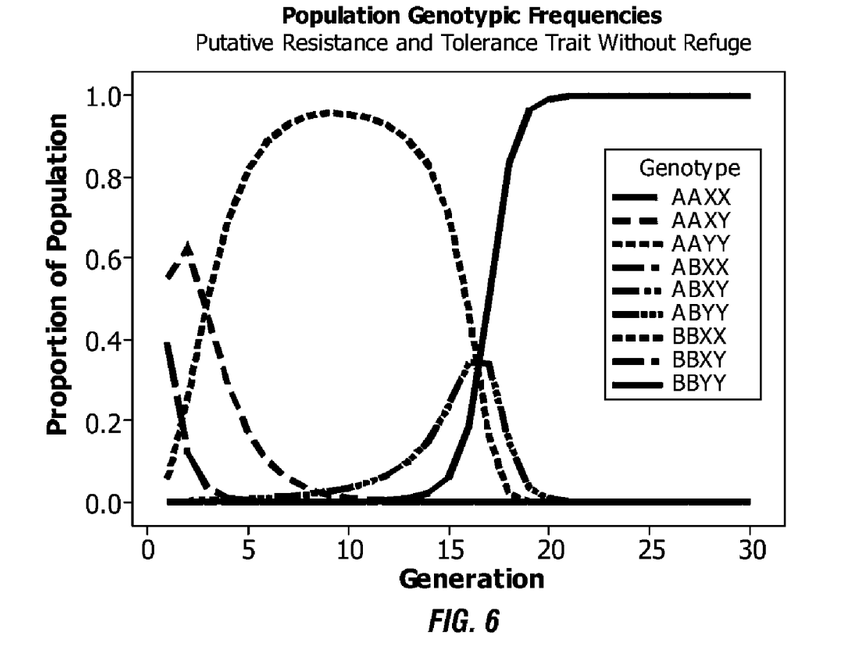
FIG. 6 shows population genotypic frequencies over generations using the WCR benchmark simulation, and excluding any block or blended refuge.

The interaction between the putative resistance gene and the tolerance trait was assessed using the same simulation described by FIG. 3, except including the tolerance trait (Y). The proportion of each genotype over generations is presented in FIG. 6. Response of the tolerance trait genotypes (XX, XY and YY) and the slope of the line predicting the proportion of individuals homozygous for Y appeared similar between this simulation and when the tolerance trait was modeled independently (FIGS. 5 and 6). The proportion of individuals with the Y allele increased very rapidly; most of this increase came from individuals homozygous susceptible for putative resistance (AAXY, AAYY) (FIG. 6). The proportion of AAXY individuals peaked in the population at 0.62 after the 2nd generation and the proportion AAYY individuals reached 0.5 by the 3rd generation, similar to the simulation with YY only described above. Individuals homozygous for Y were present at 0.9 after 7 generations. An obvious sign of interaction between Y (tolerance) and B (major resistance) alleles is evident around the 9th generation when the proportion of individuals homozygous for A and Y, which had reached approximately 0.96, began to decline at a rate similar to its earlier rate of increase (FIG. 6).

The onset of putative resistance was significantly delayed in this simulation incorporating both putative major resistance and the tolerance trait (FIG. 6). There were 3 genotypes heterozygous for putative resistance (ABXX, ABXY and ABYY); however, only the ABYY genotype occurred at levels >0.01 within the population. Both the ABXX and ABXY genotypes never reached a proportion of 0.01 in the population throughout 30 generations of simulation. This is likely explained by the higher initial frequency and additive inheritance of the Y allele compared to the initial rarity and recessive inheritance of the B allele. The rapid increase in Y allele frequency and especially AAYY individuals is the primary explanation for the delay in resistance compared to the simulation for the B allele alone (FIG. 6).

When resistance is recessive, the proportion of individuals heterozygous for putative resistance (AB) generally must increase substantially before resistance will evolve at an exponential rate. Any delay in the accumulation of heterozygous (AB) individuals, prevents homozygotes and translates into a delay in resistance. In this simulation using a recessive putative resistance gene and a more frequent and additive tolerance trait, we observe a delay in the accumulation of AB individuals (FIG. 6). The Y allele, and especially the ABYY genotype, interferes with the evolution of individuals heterozygous for the major resistance allele. This is illustrated using elements of FIGS. 3, 4 and 6. In the absence of both refuge and the tolerance trait (FIG. 3), the proportion of AB individuals increases rapidly until generation 5 where BB individuals become the most abundant genotype. In the absence of the tolerance trait and presence of a 20% block refuge, the addition of refuge individuals (AA) results in a more gradual increase in the AB genotype, which peaks at generation 14 (FIG. 4). The tolerance trait has an effect on WCR adaptation toward major resistance similar to the 20% block refuge. Thus, in the absence of refuge, but presence of the tolerance trait, the proportion of ABYY genotypes increases gradually and peak at 0.34 after generation 16 (FIG. 6). This is near generation 17 when the proportion of individuals homozygous for both B and Y reach 0.50. After generation 17, resistance evolves rapidly and fixation of the BBYY genotype occurs after 30 generations (FIG. 6). As a result, the presence of the tolerance trait with no structured refuge has essentially the same effect as a large block refuge in the absence of a tolerance trait in delaying the development of resistant pests.

The existence of a heritable trait or traits in the rootworm population, which confer a low level of tolerance to DAS-59122-7 creates surviving refuge insects (AA), which can extend durability relative to putative resistance. However, the most important effect on durability stems from the interaction between the Y allele and putative resistance and not simply the addition of A alleles from theses survivors. In these simulations, the existence of the tolerance trait increases durability by approximately 3-fold regardless of structured refuge beyond the 0.0075 off-type rate.

This simulation shows that inheritance of a tolerance trait such as the one found in the WCR surviving DAS-59122-7 maize can significantly prolong durability compared to a CRW system where there are no such tolerance traits found. This is a novel finding. In this unique situation the Y allele confers a low level of tolerance to and survival on DAS-59122-7. These survivors can act as refuge beetles by preserving A alleles; however, it is the interaction of a more frequent and additive tolerance trait that is most responsible for delaying resistance. The competitiveness of this tolerance trait already in WCR populations introduces an adaptive barrier for development of putative resistance. The delay in adaptation toward putative resistance based on effects of an independent tolerance gene is similar in function to the barrier resulting from pyramiding two insecticidal proteins with independent mechanisms of bioactivity. In these simulations, rootworm surviving as a direct result of a tolerance trait can extend durability similar to the durability provided by deploying a 20% block refuge in the absence of a tolerance trait.

This simulation data, along with the empirical data collected and described above, show that plants incorporating DAS-59122-7 do not require a separate structured refuge in order to slow the development of resistant pests, in contrast to other events where comparable tolerance traits are not inherent in rootworm populations. Further, the simulation data assumes the presence of a putative resistance gene, however no pests exhibiting such a gene have yet been identified. Accordingly, the durability of DAS-59122-7 may be even greater, for example if the development of resistance only comes about as the result of multiple gene interactions, which would most likely develop more slowly than a single resistance allele. As a result, DAS-59122-7 is well-suited for maximizing protection against rootworms by minimizing or eliminating structured refuge.

Other uses for the selected colonies would be appreciated by one of ordinary skill in the art, and such uses are contemplated in the context of the present invention. Further, while the invention has been described in terms of various specific embodiments, those skilled in the art will recognize that the invention can be practiced with modification within the spirit and scope of the claims.

What is claimed is:

1. A western corn rootworm colony exhibiting increased tolerance to event DAS-59122-7, wherein the rootworm colony is a non-diapausing, laboratory-selected colony and tolerance is conferred by a polygenic trait.

2. A western corn rootworm larva exhibiting increased tolerance to event DAS-59122-7, wherein the rootworm larva is a non-diapausing, laboratory-selected larva and tolerance is conferred by a polygenic trait.

* * * * *